United States Patent [19]

Wei

[11] Patent Number: 5,374,621

[45] Date of Patent: Dec. 20, 1994

[54] NEUROTENSIN METHOD FOR INHIBITING VASCULAR LEAKAGE

[75] Inventor: Edward T. Wei, Berkeley, Calif.

[73] Assignee: Regents of the University of California, Oakland, Calif.

[21] Appl. No.: 760,080

[22] Filed: Sep. 13, 1991

[51] Int. Cl.$^5$ .............................................. A61K 37/02
[52] U.S. Cl. ...................................... 514/14; 514/15; 514/16; 514/17
[58] Field of Search ............................... 514/15, 16, 17

[56] References Cited

U.S. PATENT DOCUMENTS

| | | |
|---|---|---|
| 3,926,756 | 12/1975 | Leeman . |
| 3,928,306 | 12/1975 | Uchiyama . |
| 4,091,090 | 5/1978 | Sipos . |
| 4,110,321 | 8/1978 | Folkers . |
| 4,425,269 | 1/1984 | Christy et al. . |
| 4,439,359 | 3/1984 | Holly, deceased et al. . |
| 4,665,157 | 5/1987 | Wright . |
| 4,716,149 | 12/1987 | Bonelli et al. . |
| 4,732,890 | 3/1988 | Bonelli et al. . |
| 4,801,612 | 1/1989 | Wei . |

OTHER PUBLICATIONS

Carraway et al., "Neurotensin and Related Peptides", Chpt. 4, *The Comparative Physiology of Regulatory Peptides*, ed. Holmgren, London: Chapmann & Hall, (1989).

Foreman et al., "Interaction of Neurotension with the Substance P Receptor Mediating Histamine Release from Rat Mast Cells and the Flare in Human Skin", *Br. J. Pharmac.*, 77, 531–539 (1982).

Araki et al., "Isolation and Structure of a New Active Peptide 'Xenopsin' on the Smooth Muscle, Especially on a Strip of Fundus from a Rat Stomach, from the Skin of *Xenopus iaevis*," *Chem. Pharm. Bull.*, 21 (12), 2801–2804 (1973).

Di Paola et al., "Cardiovascular Effects of Neurotension and Some Analogues on Rats", *European Journal of Pharmacology*, 175, 279–283 (1990).

Rivier et al., "Neurotension Analogues. Structure-Activity Relationships", *Journal of Medicinal Chemistry*, 20 (11), 1409–1412 (1977).

Granier et al., "Synthesis and Characterization of Neurotensin Analogues for Structure/Activity Relationship Studies".

*Primary Examiner*—Howard E. Schain
*Assistant Examiner*—L. Lee
*Attorney, Agent, or Firm*—Majestic, Parsons, Siebert & Hsue

[57] ABSTRACT

A method of retarding vascular leakage caused by tissue injury comprises administering a neurotensin or a neurotensin analog (SEQ ID NO: 1) at dosages sufficient to prevent or retard injury induced vascular leakage following injury or before deliberate injury.

20 Claims, 2 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( D ) TOPOLOGY: linear     ( i i ) MOLECULE TYPE: peptide     ( v ) FRAGMENT TYPE: internal     ( i x ) FEATURE:
        ( A ) NAME/KEY: Peptide
        ( B ) LOCATION: 1
        ( D ) OTHER INFORMATION: /note="Substituted by Arg or Lys."

( i x ) FEATURE:
        ( A ) NAME/KEY: Peptide
        ( B ) LOCATION: 2
        ( D ) OTHER INFORMATION: /note="Substituted by Lys, Asn, Gly, Ile, His or Arg."

( i x ) FEATURE:
        ( A ) NAME/KEY: Peptide
        ( B ) LOCATION: 4
        ( D ) OTHER INFORMATION: /note="Substituted by Trp or Tyr."

( i x ) FEATURE:
        ( A ) NAME/KEY: Peptide
        ( B ) LOCATION: 5
        ( D ) OTHER INFORMATION: /note="Substituted by Phe or Ile."

( x ) PUBLICATION INFORMATION:
        ( H ) DOCUMENT NUMBER: US 4801612
        ( J ) PUBLICATION DATE: 31-JAN- 1989

( x ) PUBLICATION INFORMATION:
        ( H ) DOCUMENT NUMBER: US 3926756
        ( J ) PUBLICATION DATE: 30-DEC- 1975

( x ) PUBLICATION INFORMATION:
        ( H ) DOCUMENT NUMBER: US 3928306
        ( J ) PUBLICATION DATE: 23-DEC- 1975

( x ) PUBLICATION INFORMATION:
        ( H ) DOCUMENT NUMBER: GB 8719248
        ( J ) PUBLICATION DATE: 24-FEB- 1988

-continued ( x ) PUBLICATION INFORMATION:
  ( H ) DOCUMENT NUMBER: US 4091090
  ( J ) PUBLICATION DATE: 23-MAY-1978

( x i ) SEQUENCE DESCRIPTION: SEQ ID NO:1:

Xaa  Xaa  Pro  Xaa  Xaa  Leu
1                 5

( 2 ) INFORMATION FOR SEQ ID NO:2:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( v ) FRAGMENT TYPE: N-terminal ( i x ) FEATURE:
    ( A ) NAME/KEY: Peptide
    ( B ) LOCATION: 1
    ( D ) OTHER INFORMATION: /note="X is pGlu."

( x ) PUBLICATION INFORMATION:
    ( H ) DOCUMENT NUMBER: US 4801612
    ( J ) PUBLICATION DATE: 31-JAN-1989

( x ) PUBLICATION INFORMATION:
    ( H ) DOCUMENT NUMBER: US 3926756
    ( J ) PUBLICATION DATE: 30-DEC-1975

( x ) PUBLICATION INFORMATION:
    ( H ) DOCUMENT NUMBER: US 3928306
    ( J ) PUBLICATION DATE: 23-DEC-1975

( x ) PUBLICATION INFORMATION:
    ( H ) DOCUMENT NUMBER: GB 8719248
    ( J ) PUBLICATION DATE: 24-FEB-1988

( x ) PUBLICATION INFORMATION:
    ( H ) DOCUMENT NUMBER: US 4091090
    ( J ) PUBLICATION DATE: 23-MAY-1978

( x i ) SEQUENCE DESCRIPTION: SEQ ID NO:2:

Xaa  Leu  Tyr  Glu  Asn  Lys  Pro
1                 5

NEUROTENSIN METHOD FOR INHIBITING VASCULAR LEAKAGE

FIELD OF THE INVENTION

This invention generally relates to a method of inhibiting vascular leakage in connection with injuries to tissues, and more particularly to the use of neurotensin and related peptides (SEQ ID NO: 1) for inhibiting vascular leakage.

This invention was made with Government support under Grant No. DA-00091 awarded by the National Institutes of Health. The Government has certain rights in this invention.

BACKGROUND OF THE INVENTION

The vascular tree of humans is about 25,000 to 60,000 miles long through which 1000 to 2000 gallons of blood are pumped each day by the heart. In the outermost peripheral bifurcations of this tree—the microcirculation—a surface area is maintained for the exchange of nutrients and the drainage of waste products between blood and tissues. After tissue injury (by chemical, physical or biological agents), the sensitive local mechanisms regulating microvascular perfusion are impaired. Vascular patency is reduced, red blood cells adhere and stack up in a phenomenon called sludging, and blood contents leak into tissues. In severe injuries, especially in the respiratory tract, these changes in the microcirculation can distort tissue architecture, impede delivery of oxygen to cells, and cause extensive fluid loss from the vascular compartment resulting in life-threatening conditions such as lung edema, electrolyte imbalance, shock and other circulatory disorders. Thus, disruption of the microcirculation is harmful, especially when there is excessive leakage of blood contents into tissues.

Earlier views of tissue injury have sometimes focused upon the signs and the symptoms of inflammation, which is signalled by redness, swelling, heat and pain. A variety of chemicals have been implicated as chemical mediators of the inflammatory reaction, including histamine, serotonin, kinins, prostaglandins, platelet-activating factors, leukotrienes, and, from nerve endings, substance P. Mediators of the acute inflammatory reaction seem to play roles in one or more of increasing vascular permeability, attracting leukocytes, producing pain, local edema and necrosis.

A variety of physiologic responses occur from the biological events that constitute the inflammatory processes, and there are various steroid and non-steroid, anti-inflammatory drugs known to the art. In order to preserve vascular integrity, research and drug developments in this field have emphasized the discovery of drug antagonists on inflammatory mediators (substances that are released by injured tissues) that cause disruption of the microcirculation. In injured tissues, however, a number of inflammatory mediators are released.

U.S. Pat. No. ,801,612, inventor Wei, issued Jan. 1, 1989, discloses the use of inhibiting an inflammatory response in the skin or mucosal membranes of a patient by administering Corticotropin-Releasing Factor ("CRF"), or its analogs. CRF acts as an anti-inflammatory agonist. That is, CRF appears to be a substance that actively shuts off the response of tissues to virtually all known inflammatory mediators. The shut-off process may be triggered by agonist actions of CRF on epithelial cell-cell and cell-substratum endothelial binding sites that activate cell-cell, cell-substratum adhesion mechanisms so that the "tightening" of cell-cell, cell-substratum junctions and matrices prevent vascular leakage. CRF belongs to the corticoliberin superfamily.

Neurotensin is a 13-amino acid residue peptide first described by Carraway and Leeman in 1973. An 8-residue peptide, named xenopsin, was discovered in frog skin at about the same time by Araki et al. (1973). The neurotensin and xenopsin peptides are structurally related and affect various physiological functions such as blood flow (producing dilatation of blood vessels and a fall in blood pressure), digestion (these peptides increase the motility of the gut), temperature regulation (central injections of these peptides produce a fall in core temperature) and antinociception (administration of these peptides reduce motor responses to noxious stimuli). Neurotensin itself releases histamine from mast cells. U.S. Pat. No. ,926,756, inventors Leemah, issued Dec. 30, 1975, discloses the hypothalamically derived substance (and a synthetically prepared tridecapeptide) designated as "neurotensin." The biological activity of neurotensin was described by observing the vasodilation in rats, and was observed to cause a marked increase in vascular permeability following intravenous injection or intradermal administration. The octapeptide designated "xenopsin" having an amino acid sequence that is similar to neurotensin, is disclosed by U.S. Pat. No. ,928,306, inventors Uchiyama, issued Dec. 23, 1975. The octapeptide so designated depresses blood pressure and causes stomach muscle contractions.

Foreman et al. studied an interaction of neurotensin with substance P, and suggested that neurotensin is a partial agonist at the substance P receptors on rat mast cells, and in human skin. *Br. J. Pharmac.*, 77:531–539 (1982). Antagonism of substance P, however, does not indicate or constitute full efficacy as an anti-inflammatory agent on injury-induced vascular leakage.

Some other members of the neurotensin family, all of which are strikingly similar in their C-terminal regions, are described by Carraway and Reinecke in their article "Neurotensin and Related Peptides", which appears as Chapter 4 in *The Comparative Physiology of Regulatory Peptides* (Holmgren, editor, Chapmann & Hall, London, 1989). As noted by Carraway and Reinecke, structure and function studies have indicated a strong dependence on the five or six residues of the C-terminal portion for neurotensin and related peptides, and it appears that the C-terminal portion of these peptides is highly conserved in evolution.

Despite the studies of various biological activities for neurotensin and peptides related to neurotensin, no researchers have reported that neurotensin, and related peptides act as anti-inflammatory agonists and, like CRF, actively shut off the response of tissues to virtually all known inflammatory mediators. Instead, neurotensin has been generally thought to be a promoter of vascular leakage in the circulatory system or has generally been thought to be an inflammatory mediator.

SUMMARY OF THE INVENTION

In one aspect of the present invention, a method of retarding vascular leakage caused by tissue injury comprises administering an effective amount of a neurotensin or a neurotensin-related peptide (SEQ ID NO:1) to the tissue.

Neurotensin-related peptides administered to animals will attenuate the swelling response to heat applied to the skin. Furthermore, neurotensin-related peptides will also protect blood vessels in the brain cortex, in the skeletal muscle and in the lower respiratory tract against injury-induced vascular leakage. Neurotensin and neurotensin-related peptides appear to have a global protective effect on the microcirculation in different vascular beds, and thus such peptides are useful in the treatment of various tissue injuries.

PREFERRED EMBODIMENTS OF THE INVENTION

Neurotensin and neurotensin-related peptides (SEQ ID NO:1) act as inhibitors of vascular leakage after tissue injuries. That is, these peptides act as anti-inflammatory agonists so that administration results in actively shutting off the response of tissues to virtually all known inflammatory mediators. For example, a dose of neurotensin and related peptides of about 10 nmol/kg i.v. will inhibit the increase in swelling of limbs by 60% to 80% after injurious stimuli such as heat. The protective effects of neurotensin and related peptides also occur in brain, lung and muscle tissues.

Because the action of neurotensin (and neurotensin-related peptides) has been found to be as anti-inflammatory agonists, a wide variety of clinical applications where one wishes to inhibit vascular leakage from various tissues after injury are possible. These peptides are suggested for clinical use with injuries to skin and mucosal membranes (eyelids, nasal membranes, oropharyngeal membranes, upper respiratory tract, esophagus, lower digestive tract, bladder), skeletal muscle, smooth muscle, cardiac muscle, blood vessels of the brain, and blood vessels of the lungs and kidneys. For example, among potential uses of these peptides are where tissues have been injured as follows.

For thermal burns, irradiation burns, for frostbite, or for other inflammatory conditions of the skin, the neurotensin and the related peptides may be used to reduce swelling, pain, and plasma extravasation.

For irritants deposited on the upper airways or in chronic allergic conditions such as asthma, the peptides may be used to decrease irritancy, bronchial inflammation, edema, and plasma extravasation.

For the lower respiratory tract, to reduce pulmonary edema from left ventricular failure, adult respiratory distress syndromes, for toxic injury to pulmonary alveoli as caused by cancer chemotherapeutic agents or environmental chemicals such as nitrogen oxides, paraquat, or ozone, the peptides may be usefully administered.

For lacerative or traumatic injuries to all tissues, such as might occur after knife wounds, surgical operations, and automobile accidents, the peptides may be used to reduce swelling, pain, and inflammation.

For tissue infarcts, which result in tissue hypoxia, ischemic anoxia and edema, such as occurs after brain strokes or myocardial infarcts, neurotensin and the related peptides may be used to reduce passage of blood constituents into the tissue matrix and enhance survival of the remaining tissues.

For preventing the actions of endogenous or exogenous chemicals that directly injure the endothelium, such as endotoxins or inflammatory mediators, resulting in the clinical condition of septic shock, the neurotensin and the related peptides may be useful in reducing the loss of blood volume.

For reducing brain edema as might occur after traumatic head injury, metastasized or primary tumors, or from intracerebral hemorrhages.

For preserving the integrity of the vascular tree of an organ prior to or during its removal for transplantation, such organs being kidneys, liver, or heart, administration of these peptides to such tissues is suggested.

The peptides may be administered intravascularly (e.g., 0.001 to 1 mg/kg) or topically (for example, by inhalation or dermal application) at dosages of 0.001 to 5 mg/kg body weight to prevent or retard injury induced vascular leakage following injury or before deliberate injury (such as during abdominal or orthopedic surgery). The peptides are preferably administered at about 5 to 10 μg/kg i.v. Thus, for example, individual or separate injections may be made or alternatively the peptides may be continuously infused for several hourly periods over a course of up to two weeks for severe conditions such as septic shock or trauma at doses at 0.01 to 1 mg/kg. The related hexapeptide neurotensins—neurotensin (8-13) and N-acetyl-neurotensin (8-13)—are particularly preferred as having minimal hypotensive activities.

The peptides may be administered in combination with a pharmaceutically acceptable carrier, such as isotonic saline, phosphate buffer solution or the like. Topical administration is also feasible since the peptides are relatively small.

Compositions and excipients useful for the administration of small peptides through the nasal mucosa are, for example, described by U.K. patent application No. 8719248, published Feb. 24, 1988, applicant Sandoz Limited. Topical compositions with enhanced penetration through intact skin preferably include a potentiator, many of which are described by U.S. Pat. No. 4,91,090, issued May 23, 1978, inventor Sipos.

The peptides form pharmaceutically acceptable salts with organic and inorganic acids and can be administered in salt form. Examples of suitable acids for the formation of pharmaceutically acceptable salts are hydrochloric, sulfuric, phosphoric, acetic, benzoic, citric, malonic, salicylic, malic, fumaric, succinic, tartaric, lactic, gluconic, ascorbic, maleic, benzene-sulfonic, methane- and ethanesulfonic, hydroxymethane- and hydroxyethane- sulfonic.

Salts may also be formed with suitable organic pharmaceutically acceptable base addition salts. These organic bases form a class whose limits are readily understood by those skilled in the art. Merely for purposes of illustration, the class may be said to include mono-, di-, and trialkylamines, such as methylamine, dimethylamine, and triethylamine; mono-, di- or trihydroxyalkylamines such as mono-, di- and triethanolamine; amino acids such as arginine, and lysine; guanidine; N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.* 66 (1): 1–19 (1977).

The peptides can be synthesized by various suitable chemical methods, preferably by solid phase synthesis, manual or automated, as first developed by R. B. Merrifield and described by J. M. Stewart and J. D. Young in "Solid Phase Peptide Synthesis" (1984). Chemical synthesis joins the amino acids in the predetermined sequence (SEQ ID NO:1) starting at the C-terminus. Basic solid phase methods require coupling the C-terminal protected alpha-amino acid to a suitable insoluble resin support. The described peptides require benzyhydrylamine (BHA) or 4-methylbenzyhydrylamine (MBHA) resins to produce the C-terminal amide upon completion. Amino acids for synthesis require protection on the alpha-amino group to ensure proper peptide bond formation with the preceding residue (or resin support). Following completion of the condensation reaction at the carboxyl end, the alpha-amino protecting group is removed to allow the addition of the next residue. Several classes of alpha-protecting groups have been described, see J. M. Stewart and J. D. Young in "Solid Phase Peptide Synthesis" (1984), with the acid labile, urethane-based tertiary-butyloxycarbonyl (Boc) being the historically preferred. Other protecting groups, and the related chemical strategies, may be used, including the base labile 9-fluorenylmethyloxycarbonyl (FMOC). Also, the reactive amino acid side-chain functional groups require blocking until the synthesis is completed. The complex array of functional blocking groups, along with strategies and limitations to their use, have been reviewed by M. Bodansky in "Peptide Synthesis" (1976), and, J. M. Stewart and J. D. Young in "Solid Phase Peptide Synthesis" (1984).

Solid phase synthesis is initiated by the coupling of the described C-terminal alpha-protected amino acid residue. Coupling requires activating agents, such as dicyclohexycarbodiimide (DCC) with or without 1-hydroxybenzo-triazole (HOBT), diisopropylcarbodiimide (DIIPC), or ethyldimethylaminopropylcarbodiimide (EDC). After coupling the C-terminal residue, the alpha-amino protecting group is removed by trifluoroacetic acid (25% or greater) in dichloromethane in the case of acid labile tertiary-butyloxycarbonyl (Boc) groups. A neutralizing step with triethylamine (10%) in dichloromethane recovers the free amine (versus the salt). After the C-terminal residue is added to the resin, the cycle of deprotection, neutralization and coupling, with intermediate wash steps, is repeated in order to extend the protected peptide chain. Each protected amino acid is introduced in excess (three to five fold) with equimolar amounts of coupling reagent in suitable solvent. Finally, after the completely blocked peptide is assembled on the resin support, reagents are applied to cleave the peptide from the resin and to remove the side chain blocking groups. Anhydrous hydrogen fluoride (HF) cleaves the acid labile tertiary-butyloxycarbonyl (Boc) chemistry groups. Several nucleophilic scavengers, such as dimethylsulfide and anisole, are included to avoid side reactions especially on side chain functional groups.

Broadly, by "neurotensin" and "neurotensin related peptides," or analogs, is meant a peptide having the primary sequence $T_N$-$A_1$-$A_2$-Pro-$A_4$-$A_5$-Leu-$T_C$ (SEQ ID NO:1) where $A_1$ is Arg or Lys, $A_2$ is Lys, Ash, Gly, Ile, His, or Arg, $A_4$ is Trp or Tyr, $A_5$ is Phe or Ile, $T_N$ is an amino terminal portion, and $T_C$ is a carboxyl terminal portion. More preferably, $T_N$ will be N-acetyl, pyroglutamyl-glycinyl or pGlu-Leu-Tyr-Glu-Asn-Lys-Pro (SEQ ID NO:2), while $T_C$ will be carboxyl or a pharmaceutically acceptable salt thereof. It is believed that $T_N$ should have not more than about seven amino acid residues (since neurotensin itself has seven in the $T_N$ portion of the molecule), and generally smaller members of the family may be preferred due to fewer side effects. Generally, $T_N$ will be chosen to enhance absorption, to reduce side effects, and to increase selectivity for anti-inflammation. The $T_C$ carboxyl terminal may include the pharmaceutically acceptable salts (as already described), but preferably is not amidated because amidation has been found to lead to loss of activity.

EXPERIMENTAL

Heat Injury to the Skin

To evaluate the ability of neurotensin and related peptides (SEQ ID NO:1) to reduce edema after heat injury, we immersed the paws of anesthetized rats in warm water (58° C.) for 1 minute and, subsequently, measured the changes in paw volume and increases in water content. These general methods have been described in more detail elsewhere (see Wei et al., *J. Pharmacol. Exp. Ther.*, 247: 1082–1085, 1988). Peptides, obtained from Peninsula Laboratories or Bachem Laboratories, were dissolved in sterile saline and injected intravenously 10 minutes before exposure to heat.

Figure 1:
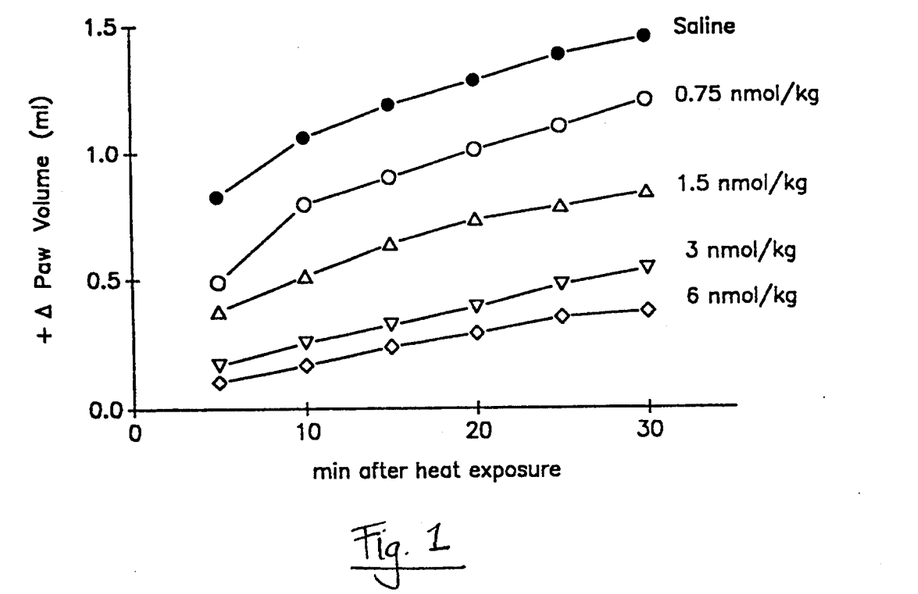
FIG. 1 graphically illustrates an experiment in which either a saline control dose or different dosages of neurotensin or a neurotensin related peptide (SEQ ID NO: 1) were administered to an animal paw and the volume of the paw measured. The paw was then exposed to 58° C. water and removed from the hot water. The vertical axis is paw volume change from the initial volume, while the horizontal axis is minutes after heat exposure. The particular neurotensin for which data is here illustrated was neurotensin (8-13).
Figure 2:
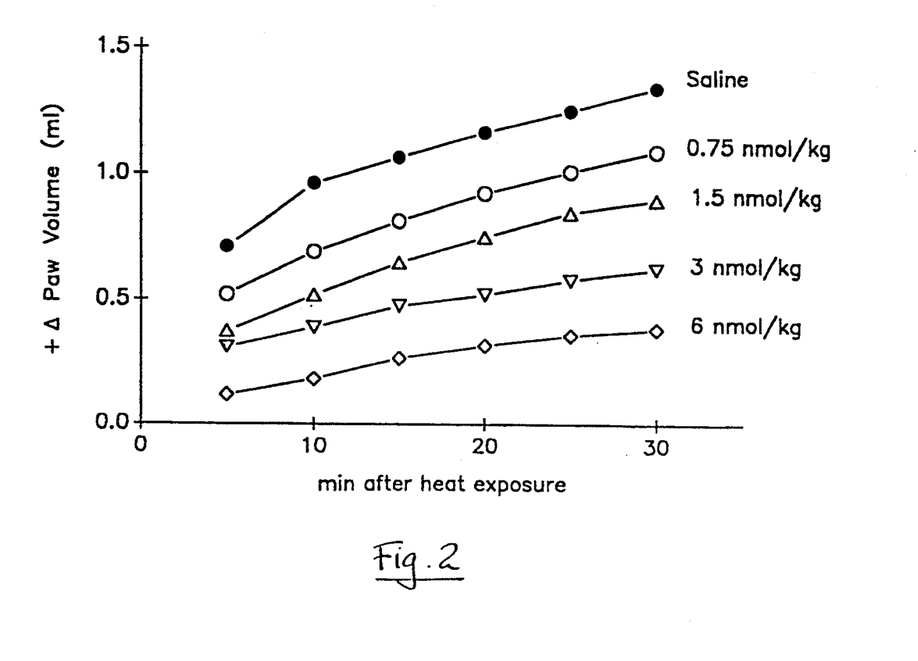
FIG. 2 is similar to the graphical illustration of FIG. 1 (and the data was similarly obtained), but the particular neurotensin related peptide used was N-acetyl-neurotensin (8-13).
Figure 3:
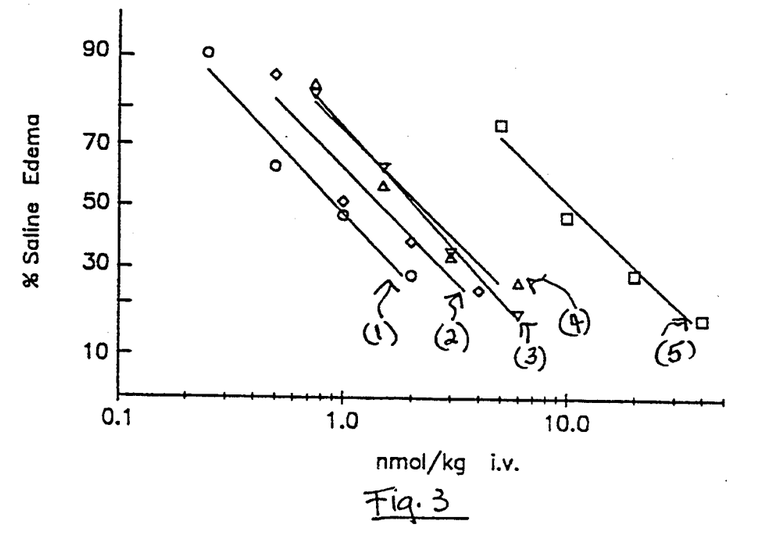
FIG. 3 graphically illustrates the log-probit dose response curves for five peptides of the neurotensin family on heat induced edema in rat paws where the data with compound (1) was with xenopsin, with compound (2) was neurotensin, with compound (3) was with neurotensin (8-13), with compound (4) was with N-acetyl-neurotensin (8-13), and with compound (5) was neuromedin N, the doses being on a scale of nmol/kg body weight, administered i.v., and the vertical axis being percent of edema with respect to a saline control.

A typical experiment with neurotensin (8-13) is shown in FIG. 1. After removal of the saline-treated animal's paw from 58° C. water, the paw's skin became red, followed by progressive swelling from an initial volume of about 1.5 ml to a net increase of 0.77 ml within 5 minutes. After 30 minutes, the saline-treated group had paw volumes that increased by 1.41 ml. Thus, neurotensin (8-13) produced a dose-dependent suppression of the swelling response.

To compare the potency of the peptides, the following method was used. Thirty minutes after heat injury, rats were killed with an over-dose of concentrated sodium pentobarbital, and both paws cut off at the ankle joint and weighed. All paws were then dried in an oven at 80° C. for 24 hours and re-weighed to obtain % increase in water content as:

$$\frac{\text{(wet wt. of heated paw} - \text{dry wt. of heated paw)}}{\text{(wet wt. of unheated paw} - \text{dry wt. of unheated paw)}} =$$

% water increase

The abilities of peptides to inhibit edema, as a % of the saline-treated control group, was plotted and the median effective dose (ED50) of each peptide was calculated. As can be seen from the results in the Table 1, xenopsin and neurotensin-related peptides are potent inhibitors of edema, being effective at microgram doses.

TABLE 1

Anti-Inflammatory Potency of Xenopsin, Neurotensin and Other Peptides on Heat Injury

| | Dose Range (nmol/kg) | ED50 (nmol/kg) | ED50 (µg/kg) |
|---|---|---|---|
| Xenopsin | 0.25–2.0 | 0.9 | 0.88 |
| Neurotensin (NT) | 0.50–4.0 | 1.5 | 2.5 |
| NT (8-13) | 0.75–6.0 | 1.9 | 1.6 |
| N-Ac-(8-13) | 0.75–6.0 | 2.1 | 1.8 |
| Neuromedin N | 5–40 | 10.0 | 7.5 |
| Kinetensin | 200–800 | ED20: 420 = 492 µg | |

LANT-6, a hexapeptide neurotensin fragment found in chickens, is also active in inhibiting heat-induced edema. A dose of 0.5 mg/kg i.v. reduced swelling from 69±2% to 2±1% (N=6 pairs, P<0.001). The above data show that these peptides are capable of inhibiting swelling in skin. Additional studies were conducted which demonstrated that these peptides also inhibit swelling in mucosa of the esophagus, trachea, bladder, and in skeletal muscle, lung and brain (see data below). It has thus been shown that these peptides have a wide spectrum of anti-inflammatory activities.

EXAMPLE 2

Experiments were conducted on 260±6 (S.D.) male Sprague-Dawley rats from Simonsen Laboratories (Gilroy, Calif.). Animals were injected with sodium pentobarbital, 60 mg/kg i.p. Ten to 15 minutes later, after anesthesia was signaled by loss of the righting reflex and motor responses to tail pinch, Monastral blue B (used to estimate leakage of macromolecules from blood vessels), suspended in saline at 30 mg/ml (Sigma Co., St. Louis, Mo.), was injected 60 mg/kg i.v. at a rate of approximately 0.2 ml/100 g body weight/min into a branch of the femoral vein. Procedures for inducing vascular leakage began three minutes after Monastral blue infusion.

Skeletal Muscle Injury

The abdomen was shaved and a 4 cm scalpel cut was made in the midline. After manually parting the skin, an incision of equal length was made in the rectus abdominus and the skin was then pushed together to cover the wound. Thirty minutes after celiotomy, the rat was euthanized with an i.v. overdose of pentobarbital and the skin and muscle surrounding the site of incision were removed and fixed in 10% neutral-buffered formalin (NBF) for at least 2 days before further analysis.

Cerebral Cortex (Brain) Injury

This model of vasogenic edema in brain tissues was first described by Chan et al. (1983). Anesthetized rats were mounted on a David Kopf stereotaxic instrument and a 2 to 2.5 cm midline incision made in the shaved scalp. After parting the skin and connective tissue to expose the skull, a 60 $mm^2$ plate, connected to a brass cup filled with dry ice and acetone and maintained at −50° C., was applied to the skull for four minutes. One hour later, the animal was perfused through the aorta with saline, followed by 10% NBF, and then the brain was removed and stored in 10% NBF for at least two days before further analysis. Sections of membranes covering the cortex were also dissected from the underlying tissues and separately examined.

Quantifying Vascular Leakage

To measure the area of dye distribution and the intensity of dye staining on the surfaces of the tissues, we used an image-processing system (JAVA, Jandel Video Analysis System, Corte Madera, Calif.) in which a video image, composed of pixels with different gray intensities, was subjected to numeric analysis. Samples of the abdominal muscle and brain were placed on a non-reflective coated glass board illuminated by six 60 watt fluorescent bulbs placed 1.65 m above the tissues and the images recorded under these constant conditions, without magnification, on video film. The areas of dye distribution were demarcated with a mouse-pointer device and the average intensity in the defined areas was obtained. To calibrate light intensity on the JAVA system, various concentrations of Monastral blue B (0.0625 to 16 mg/ml) were placed on white filter paper and the intensity scale set from 0 to 255 units. The relationship of light intensity, which is the degree of blueness in arbitrary units, to Monastral blue B concentrations (mg/ml) was: light intensity =124+116 log MB, an equation obtained by linear regression with a correlation coefficient of r=0.98. The term "lesion size", applied to the area of staining multiplied by its light intensity, represents a two-dimensional measurement of vascular leakage. This assessment was considered adequate because the injuries were to the surfaces of the muscle and cortex and the lesions were not more than a few mm deep. To further characterize the sites of dye leakage from blood vessels, samples of muscle and cortex, cut to approximately 500 µm thickness, were mounted in glycerol gelatin for microscopic examination.

Drugs Used and Statistics

Xenopsin, neurotensin and neurotensin-related peptides (SEQ ID NO:1) (synthesized by solid-phase methods and purified to >95% by high-pressure liquid chromatography) were purchased from Peninsula Laboratories (Belmont, Calif.) or Bachem Corp. (Torrance, Calif.) and dissolved in sterile saline for injection. Animals were randomly assigned to treatments using a paired control design with a minimum of 6 rats per group. Data were expressed as the mean ± S.E.M. and the ED50 and 95% confidence limits were estimated by the method of Litchfield and Wilcoxon (1949). The Student's test was used for comparison of groups.

Results.

Within minutes after celiotomy, a bluish tinge appeared on the surface of the abdominal muscle and the surrounding skin, progressing to a stain of about 750 to 850 $mm^2$ after 30 minutes. Microscopy revealed that the blueness was due to leakage of Monastral blue dye from small blood vessels with diameters up to 15 µm and having the typical pattern seen in skeletal muscle tissues. In some specimens, the pigment diffused from the vessels into the tissue matrix. N-Acetyl neurotensin (8-13), 4 nmol/kg i.v., injected 10 minutes before or 5 minutes after celiotomy significantly reduced the area and intensity of dye staining (Table 2) when compared with the respective saline groups.

Injury to the brain cortex by freezing produced a dye stain of approximately 38 mm$^2$. Under the microscope, the blue dye could be seen embedded in the walls of small blood vessels of the cortex. N-Acetyl neurotensin (8-13), 4 nmol/kg i.v., injected 10 minutes before freeze injury, decreased the area and intensity of dye leakage and reduced the overall lesion size (Table 3). The inhibition of dye leakage occurred in the meninges as well as in the superficial layers of the cortex.

TABLE 2

N-Acetyl-Neurotensin(8-13) [AcNT8-13] Inhibits Vascular Leakage from Abdominal Muscle after Celiotomy

| Time (min) | | Area (mm$^2$) | Intensity | Lesion Size (x104) |
|---|---|---|---|---|
| −10 | SAL | 852 ± 27 | 149 ± 2 | 12.7 ± 0.4 |
|  | AcNT8-13 | 399 ± 18* | 126 ± 2 | 5.0 ± 0.2* |
| +5 | SAL | 758 ± 39 | 137 ± 31 | 10.4 ± 0.5 |
|  | AcNT8-13 | 493 ± 27* | 108 ± 5* | 5.3 ± 0.4* |

Saline (SAL), or AcNT8-13, 4 nmol/kg i.v. was injected 10 minutes before or 5 minutes after celiotomy. Muscle samples were taken 30 minutes after celiotomy, the area of blue-stained tissues and its color intensity were measured by an image-analysis system. Data represent the mean ± S.E.M.
*$P < 0.01$ vs saline control, N = 6 to 8 per group (Student's t-test).

TABLE 3

N-Acetyl-Neurotensin(8-13) [AcNT8-13] inhibits vascular Leakage from Brain Cortex After Freeze Injury

| Treatment | Area (mm$^2$) | Intensity | Lesion Size (x103) |
|---|---|---|---|
| Saline | 38 ± 2 | 151 ± 4 | 5.7 ± 0.2 |
| AcNT8-13 | 21 ± 2* | 119 ± 4 | 2.4 ± 0.3* |

Saline or AcNT8-13 4 nmol/kg i.v. was injected 10 minutes before freeze injury to the brain cortex. Sixty minutes later the brain was perfused and removed for image analysis. Data represent the mean ± S.E.M.
*$P < 0.01$ vs saline, N = 8 per group (Student's t test).

EXAMPLE 3

Lung Injury

Acute pulmonary edema can be produced within minutes in rats after intravenous injection of epinephrine (Epi). Meltzer, who first described this phenomenon in 1904, explained the edema as arising from the rapid redistribution of blood from the systemic into the pulmonary circulation. The increases in pulmonary microvascular pressure are transient, but thought sufficient to directly injure the endothelium of small blood vessels, resulting in increased vascular permeability and hemorrhage. This type of "pressure" edema represents hydraulic damage to the delicate membranes of the lower respiratory tract.

Male Sprague-Dawley rats weighing 260±9 g (Simonsen Labs, Gilroy, Calif.) were used in all experiments. Animals were anesthetized with sodium pentobarbital, 60 mg/kg i.p., and then injected with saline or neurotensin, neurotensin (8-13), or N-acetyl--neurotensin (8-3), 10 nmol/kg i.v. 10 minutes before 1-Epi bitartrate, 10 μg/kg i.v. (equivalent to 30 nmol/kg base, all doses refer to the bitartrate salt). This single dose of Epi is sufficient to produce a non-lethal pulmonary edema in the pentobarbital-anesthetized rat. Thirty minutes after Epi, animals were euthanized with concentrated pentobarbital and the lungs were removed. The magnitude of lung edema was estimated according to the procedures of Poulsen (1954). Lungs were blotted on paper towels and weighed (wet wt.), then placed in a 80° C. oven for 24 hour and re-weighed again (dry wt.). The value 1000 (wet wt.-dry wt.)/body wt. was termed the edema index.

All data are presented as mean ± SEM. Statistical significance was assessed by analysis of variance (ANOVA) with the Studentized range-test.

Results

Injection of Epi bitartrate, 10 μg/kg i.v., into anesthetized rats produced labored breathing and the development of pulmonary edema: the edema index for saline-injected rats was 3.6±0.1 (N=6) and in Epi-treated rats was increased to 6.2±0.3. Relative to normal animals of similar body weight, the Epi injection had induced a 72% increase in lung weights within 30 minutes. Neurotensin, neurotensin (8-13) and N-acetyl-neurotensin(8-13) inhibited the development of pulmonary edema as shown in Table 4.

TABLE 4

Neurotensin and Related Peptides Inhibit Epinephrine-Induced Pulmonary Edema

| Treatments | Edema Index |
|---|---|
| Saline + Saline | 3.6 ± 0.1 |
| Saline + Epi | 6.2 ± 0.3 |
| Neurotensin + Epi | 4.0 ± 0.1* |
| Neurotensin (8-13) + Epi | 4.7 ± 0.2* |
| N-Ac-Neurotensin(8-13) + Epi | 4.9 ± 0.2* |

Peptides were injected 10 nmol/kg i.v. 10 minutes before 1-epinephrine bitartrate 10 μg/kg i.v. Lungs were removed 30 minutes after Epi.
*$P < 0.01$ vs Saline + Epi group, one-way Analysis of Variance and Studentized Range test.

Antagonism of substance P is not sufficient to prevent heat-induced edema. Snider et al. have described a new potent antagonist of substance P (Science, 251: 435–437, January, 1991) called CP-96,345. However, this compound is not sufficiently active to prevent vascular leakage in bioassays, as shown by the data of Table 5 and as described by Example 4.

EXAMPLE 4

Using a randomly-paired experimental design, saline or the Pfizer substance P antagonist (CP-96,345) was injected intravenously at 4 mg/kg (dissolved in saline 4 mg/ml) 10 minutes before immersion of the pentobarbital-anesthetized rat's right paw in 58° C. water for one minute. The rat was euthanized 30 minutes later with concentrated pentobarbital and both paws removed by cutting at the ankle joint and weighed. The paws were then dried at 80° C. for 24 hours. Controls received only saline at 0.1 ml/kg i.v. The increase in the water content of the heated paw was calculated as: heated paw (wet wt.—dry wt.)—unheated paw (wet wt.—dry wt.). Data represent the mean ± S.E.M. The two groups are not significantly different (N=8 per group, Student's t test). The data is summarized in Table 5.

TABLE 5

The Potent Substance P Antagonist (CP-96,345) Does Not Prevent Vascular Leakage In Skin After Heat Injury

| Treatment | Increase in Water Content of Heated Paw (mg) |
|---|---|
| Saline | 1117 ± 33 |
| CP-96,345 | 1057 ± 24 |

In a separate experiment, the compound CP-96,345 was shown to prevent salivary secretion in the rat induced by substance P injections (40 μg/kg s.c.). Thus, a chemical (Such as illustrated by CP-96,345) that antagonizes the inflammatory mediator, substance P, is not sufficient to prevent edema after thermal injury.

EXAMPLE 5

Figure 4:
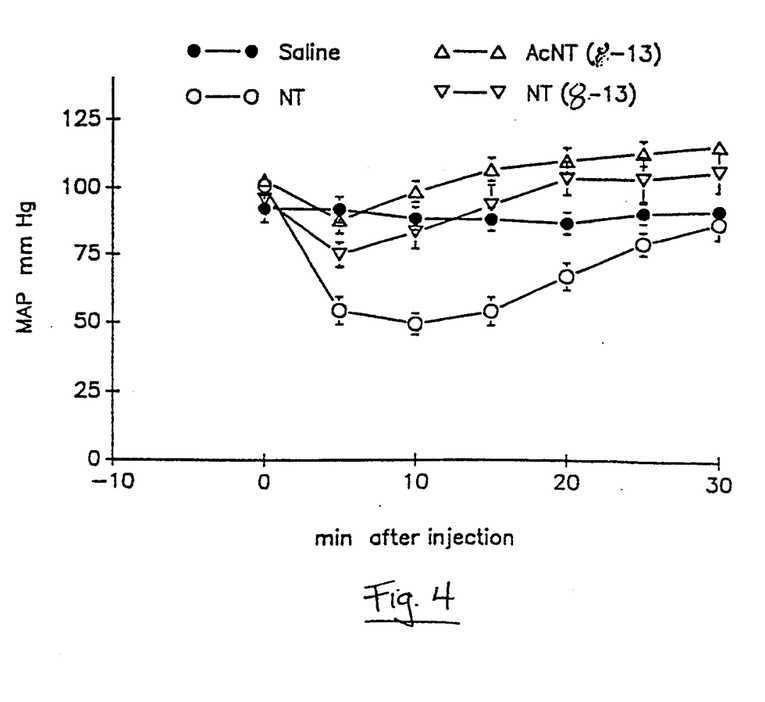
FIG. 4 graphically illustrates the effect of four peptides of the neurotensin family on blood pressure as a function of time after ten nmol/kg had been injected i.v. (where the blood pressure was measured as mean arterial pressure by mm/Hg).

A hypotensive vasodilator can exert a false impression of anti-inflammatory effect by reducing blood flow in tissues to such an extent that edema will not take place. Furthermore, hypotensive activity would be undesirable in the therapeutic use of an anti-inflammatory agent because perfusion (and oxygen delivery) may be compromised in situations where oxygen deficiency in the injured tissues will be harmful. The hypotensive activities of neurotensin and two of its shorter fragments were therefore compared. Blood pressure was monitored of animals to which 10 nmol/kg of different compounds were administered i.v. One administration was of saline as control. Another administration was of neurotensin, yet another was of AcNT (8-13), and yet another of neurotensin (8-13). Blood pressure was monitored at intervals over a thirty minute period after injection. As can be seen by the data graphically illustrated in FIG. 4, the two hexapeptide neurotensin related compounds lacked hypotensive effect so that blood pressure of the test animal over a 30 minute period after injection remained substantially constant. By contrast, the 13 amino acid peptide, neurotensin, was found to cause substantial lowering of blood pressure following administration. Although the hypotensive activity of neurotensin was expressed, the two hexapeptides tested were shown to have weak hypotensive activity (and also found to exert anti-edematogenic properties when blood pressure is not lowered). Thus, neurotensin (8-13) and N-acetyl-neurotensin (8-13) have desirable anti-inflammatory activities, which are unrelated to changes in blood flow of the injured tissues. The limited hypotensive activities of these hexapeptides make these compounds particularly preferred for various therapeutic applications.

It is to be understood that while the invention has been described above in conjunction with preferred specific embodiments, the description and examples are intended to illustrate and not limit the scope of the invention, which is defined by the scope of the appended claims.

---

It is claimed:

1. A method of retarding vascular leakage caused by tissue injury comprising:
    administering an effective amount of a peptide to tissues, the peptide being a neurotensin or neurotensin analog and having the primary sequence $T_n$-$A_1$-$A_2$-Pro-$A_4$-$A_5$-Leu-$T_c$ (SEQ ID NO:1) where $A_1$ is Arg or Lys, $A_2$ is Lys, Asn, Gly, Ile, His or Arg, $A_4$ is Trp or Tyr, $A_5$ is Phe or Ile, $T_N$ is an amino terminal portion, and $T_c$ is a non-amidated carboxyl terminal portion.

2. The method as in claim 1 wherein $T_n$, includes N-acetyl or one or more amino acid residues up to about seven amino acid residues.

3. The method as in claim 1 wherein $T_c$ is carboxyl or a pharmaceutically acceptable salt.

4. The method as in claim 1 wherein the administering is to a mammal and is at least one dose of from about 1 to about 200 µg/kg body weight.

5. The method as in claim 1 wherein the peptide is administered with a pharmaceutically acceptable carrier.

6. The method as in claim 1 wherein the administering is to a mammal and is intravascular or topical.

7. The method as in claim 6 wherein the administering is intravascular in an amount of from about 0.001 mg/kg to about 1 mg/kg body weight.

8. The method as in claim 1 wherein the peptide is administered to a mammal and is continuously infused for several hours at a dose between about 0.01 mg/kg to about 1 mg/kg body weight.

9. A therapeutic method comprising:
    administering a peptide composition to a patient in an amount effective to retard injury induced vascular leakage, the peptide composition consisting essentially of the moiety of the formula -$A_1$-$A_2$-Pro-$A_4$-$A_5$-Leu- (SEQ ID NO:1) where $A_1$ is Arg or Lys, $A_2$ is Lys, Asn, Gly, Ile, His or Arg, $A_4$ is Trp or Tyr, $A_5$ is Phe or Ile.

10. The method as in claim 9 wherein the administering is intravascular and in an amount of from about 0.001 mg/kg to about 1 mg/kg body weight.

11. The method as in claim 9 wherein the peptide administered includes neurotensin (8-13) or N-acetyl-neurotensin (8-13) (SEQ ID NO:1).

12. The method as in claim 9 wherein the administering is substantially without causing hypotension.

13. The method as in claim 11 wherein the peptide is continuously infused for several hours at a dose between about 0.01 mg/kg to about 1 mg/kg body weight.

14. The method as in claim 1 or 3 wherein the $T_N$ portion is effective to enhance absorption or to increase anti-inflammation selectivity.

15. The method as in claim 14 wherein $T_N$, includes N-acetyl, pyroglutamyl-glycinyl or pGlu-Leu-Tyr-Glu-Asn-Lys-pro (SEQ ID NO:2).

16. The therapeutic method of retarding vascular leakage in a patient caused by tissue injury comprising:
administering at least one dose of from about 1 to about 200 µg/kg body weight to the patient of a neurotensin or neurotensin analog or a pharmaceutically acceptable salt thereof.

17. The therapeutic method as in claim 16 wherein the dose is administered intravascularly or topically.

18. The therapeutic method as in claim 17 wherein the dose is administered by continuous infusion.

19. The therapeutic method as in claim 17 wherein the dose includes neurotensin (8-13).

20. The therapeutic method as in claim 17 wherein the dose includes N-acetyl-neurotensin (8-13).

* * * * *